(12) United States Patent
Maraccini

(10) Patent No.: US 8,252,335 B2
(45) Date of Patent: *Aug. 28, 2012

(54) HEALING POWDER AND METHOD OF USE THEREOF

(76) Inventor: Philip A. Maraccini, Harrison, NY (US)

( * ) Notice: Subject to any disclaimer, the term of this patent is extended or adjusted under 35 U.S.C. 154(b) by 1013 days.

This patent is subject to a terminal disclaimer.

(21) Appl. No.: 11/938,147

(22) Filed: Nov. 9, 2007

(65) Prior Publication Data

US 2008/0107734 A1 May 8, 2008

Related U.S. Application Data

(63) Continuation of application No. 11/385,265, filed on Mar. 21, 2006, now Pat. No. 7,294,350.

(51) Int. Cl.
*A61K 9/14* (2006.01)
*A61K 8/73* (2006.01)
*A61K 31/74* (2006.01)

(52) U.S. Cl. .................. 424/489; 424/70.13; 424/78.08; 514/53

(58) Field of Classification Search .................. None
See application file for complete search history.

(56) References Cited

U.S. PATENT DOCUMENTS

| | | | | |
|---|---|---|---|---|
| 6,001,385 A | * | 12/1999 | Van De Wijdeven | 424/422 |
| 6,086,869 A | * | 7/2000 | Uyama et al. | 424/85.5 |
| 7,537,832 B2 | * | 5/2009 | Carlucci et al. | 428/402 |
| 2004/0153040 A1 | * | 8/2004 | Martineau et al. | 604/304 |

FOREIGN PATENT DOCUMENTS

| | | | |
|---|---|---|---|
| CN | 1133172 A | * | 10/1996 |
| GB | 2274988 A | * | 8/1994 |
| GB | 2365443 A | * | 2/2002 |

OTHER PUBLICATIONS

Sugar—Types of Sugar. What is Confectioners' Sugar—What is Powdered Sugar—What is Icing Sugar—What is 10X Sugar.*
Full English Translation Yakoflievch et al. CN 1133172, published Oct. 16, 1996.*
Sugar—Types of Sugar. What is Confectioners' Sugar—What is Powdered Sugar—What is Icing Sugar—What is 10X Sugar (downloaded Aug. 8, 2010.*

* cited by examiner

*Primary Examiner* — Michael G Hartley
*Assistant Examiner* — Nabila Ebrahim
(74) *Attorney, Agent, or Firm* — Steven M. Hoffberg; Ostrolenk Faber LLP

(57) ABSTRACT

A wound healing powder, comprising a sugar selected from the group consisting of one or more pharmaceutically acceptable monosaccharides and disaccharides, in an amount of at least 25% by weight of the powder mixture; and an absorbent agent which forms a bioabsorbable biocompatible matrix with wound secretions, comprising a polymer formed of one or more of saccharide or saccharide derivative monomers and lactic acid monomers, in an amount of at least 25% by weight of the powder mixture.

22 Claims, No Drawings

HEALING POWDER AND METHOD OF USE THEREOF

RELATED APPLICATIONS

The present application is a Continuation of U.S. patent application Ser. No. 11/385,265, filed Mar. 21, 2006, now U.S. Pat. No. 7,294,350, the entirety of which is expressly incorporated herein by reference.

BACKGROUND OF THE INVENTION

1. Field of the Invention

The present invention relates to the field of wound dressings, and more particularly to powders which assist in wound healing.

2. Prior Art

Cornstarch has been known as a soothing and drying agent for irritated skin, such as diaper rash. Cornstarch is a dextrin, and contains amylase.

The Dressings Times, Vol. 3, No. 2, discusses wound dressings which employ sugar pastes. (www.smtl.co.uk/WMPRC/DressingsTimes/vol3.2.txt). It reports that, in 1976, Herszage and Montenegro of Argentina used ordinary sugar to treat the wounds of two patients with post-surgical necrotic cellulitis. Further successes followed and in 1980 they reported on the use of sugar paste in 120 infected wounds and recorded a cure rate of 99.2%.[1] The time taken for the wounds to heal varied between 9 days and 17 weeks, but it was observed that odor and secretion began to diminish within 24 hours and disappeared totally after 72 to 96 hours of treatment. In 1985, Trouillet et al[2] described the use of sugar in the treatment of 19 patients with acute mediastinitis following cardiac surgery. Wounds were packed every 3 to 4 hours with ordinary commercially available granular sugar (sucrose). The authors noted near complete debridement followed by the rapid formation of granulation tissue and eradication of bacterial infection after an average of 7.6 days of treatment.

Sugar was first used as a dressing in Northwick Park Hospital in 1982 when it was placed into infected radical vulvectomy wounds that had not responded to more conventional therapies. However, due to the nature of such wounds, packing with granular sugar was found to be impossible and therefore a thick paste was developed. Other early patients to be treated with sugar at Northwick Park were two hypo-gamma-globulinaemic individuals who had developed extensive tracking sinuses. For these, a thin paste was formulated that could be injected into the narrow wounds.

Thick sugar paste has a consistency similar to that of modeling clay and can be molded in the gloved hand immediately prior to packing into cavities with large openings such as pressure sores. Thin sugar paste resembles thin honey; it is suitable for instillation into cavities with small openings with a syringe and fine plastic tube or catheter.

| Formulae for sugar pastes (Prior Art) | | |
|---|---|---|
| | Thin | Thick |
| Caster sugar (fine granular sucrose) | 1200 g | 1200 g |
| Icing sugar - additive free (powdered sucrose) | 1800 g | 1800 g |
| Polyethylene glycol 400 | 1416 ml | 686 ml |
| Hydrogen Peroxide 30% | 23.1 ml | 19 ml |
| (Final concentration of hydrogen peroxide is 0.15% v/w.) | | |

The pastes are prepared in the hospital pharmacy by combining the $H_2O_2$ with the PEG 400 and then incorporating this solution into the sugars with the aid of a mechanical mixer.

When homogenous the paste is packed into screw capped plastic containers and stored at 4 C. The pastes are chemically stable for at least 6 months from preparation.

Polyethylene glycol (PEG) 400 was chosen as the lubricant because it does not interact with other components of the paste and is used in a variety of pharmaceutical preparations. It is a synthetic polymer that is also used in the cosmetic industry and has significant anti-bacterial properties.[3][4] Polyethylene glycol 400 can be absorbed from mucous membranes and high blood levels may be nephrotoxic.[5] Although no toxic effects have been noted in our patients, many of whom are elderly and frail, sugar paste should be used with care in patients with impaired renal function as any absorbed polyethylene glycol is excreted renally.

Sugar paste has been used on most wound types but it has been found to be particularly effective for treating infected and malodorous wounds. Twice daily application are advised to provide the optimum antibacterial effect. This has been demonstrated both in patients with malodorous wounds (when the smell of infected necrotic tissue is removed after 2-3 days), and in patients with infected abscesses. Irrigation with thin sugar paste has achieved successful results in patients with chronic discharging sinuses who had previously failed to respond to other therapies. Repeated application over 3 to 6 weeks is generally required to bring about complete healing. Sugar paste lowers the pH of wounds to approximately 5 which may be important in infected wound although the paste does not stimulate or retard granulation tissue formation in clean wounds in the pig model.[6]

Sugar paste (thick and thin) is rapidly bactericidal against all organisms so far tested when challenged according to a modified British Pharmacopoeia antimicrobial preservatives effectiveness test. When samples of the paste were inoculated with *Staphylococcus aureus, Streptococcus faecalis, Escherichia coli* or *Candida albicans*, to give $10^5$ cfu/gram, less than 10 cfu/gram were detectable after 1 hour at 25 C.[7] Pastes diluted with serum have a reduced bactericidal effect −75% paste in serum gave an 80% reduction in viable numbers of *S. aureus* within 2 hours and a 99% reduction in viable numbers of *Proteus mirabilis* within 1 hour[3].

Although the application of sugar to a wound creates an environment with low water activity (aw) and high osmotic pressure, overall the wound remains moist. (The water activity of a solution is the ratio of its water vapour pressure to that of pure water at the same temperature so that aw=P/Po).

The effect of reducing water activity values on the growth of bacteria has been investigated by Chirife et al[8] who determined the limiting water activities at which different species of bacteria will grow. We have determined the water activity of our pastes, at different dilutions in serum, by measuring water vapour pressure at 25 C with an electronic hygrometer. Undiluted pastes have an almost zero availability of water because the sugar (sucrose) is dispersed in Polyethylene glycol 400 which does not contain water. Sugar has an osmotic action which can be thermodynamically related to water activity by the following equation:[8]

$$O = (RT/V) \times \log(1/aw),$$

where O is the osmotic pressure,
R is the gas constant,
T is the absolute temperature in degrees Kelvin,
V is the partial molal volume of water, and
aw is the water activity.

Thus, by determining water activity, the osmotic pressure can be calculated. From this equation it will be seen that a solution of low water activity has high osmotic pressure.

Because of the difficulty of conducting a controlled trial of sugar paste in human wounds, an animal study has been conducted[6] using a method similar to that reported by Winter and Scales.[9] Full thickness wounds 25 mm square, and 9 mm deep were made in the backs of pigs and around each was placed a colostomy stoma ring. This in turn was covered with a semipermeable plastic film dressing (Opsite) so as to form a moist chamber. Wounds were either covered with Opsite alone, or packed with thick sugar paste or cotton gauze soaked in various antiseptic solutions and then covered in Opsite. The results showed that there was no significant difference between wounds left unpacked, but covered with Opsite, and those Opsite covered wounds packed with sugar paste, indicating that although sugar paste did not stimulate the formation of granulation tissue, neither did it cause inhibition or toxicity. However, all wounds packed with antiseptics showed evidence of delayed healing, especially those containing chlorhexidine gluconate 0.2%. The pig model wounds were not infected so no conclusions can be drawn on the relative value of Opsite and sugar paste for healing infected wounds.

Dressing Times concluded that sugar paste should be considered for the management of all infected and malodorous wounds. It is a far less expensive alternative to Debrisan and similar products which are of dubious efficacy and are often difficult to remove from wounds. Sugar paste was also considered superior to charcoal dressings for treating malodorous wounds as it removes the cause of the smell and in this respect is similar to metronidazole gel. However sugar paste may be preferable to metronidazole gel for treating such wounds as the use of topical antibacterials and antibiotics should be avoided.[10]

Sugar paste lacks the toxicity of most antiseptics and it does not disrupt the architecture of the healing wounds, as does packing with gauze.

The paste is self-sterilizing and can be produced in different viscosities to suit all kinds of wound and it is not painful to apply. It may cause bleeding when granulation tissue is well formed, at which stage simple, non-impregnated dressings should be applied which will keep the wound moist and allow epithelialisation to occur.

REFERENCES

1. Herszage L. et al., Tratamiento de las heridas supuradas con azucar granulado comercial, Biol Trab Soc Argent., 1980, 41, 315-330.
2. Trouillet J. L., et al., Use of granulated sugar in treatment of open mediastinitis after cardiac surgery, Lancet, 1985, 2, 180-183.
3. Ambrose U. An investigation into the mode of action of Northwick Park Hospital sugar pastes. Hatfield Polytechnic, 1986, B. Sc. Applied Biology Thesis.
4. Chirife J., et al., In-vitro antibacterial activity of concentrated polyethylene glycol 400 solutions, Antimicrob. Ag. Chemother., 1983, 24, 409-412.
5. Wilson C. G. and Thomas N. W. Interaction of tissues with polyethylene glycol vehicles Pharm. Int., 1984, 5 94-97.
6. Archer H. G. et al., A controlled model of moist wound healing: comparison between semi-permeable film, antiseptics and sugar paste. J. exp. Path., 1990, 75, 155-170.
7. Gordon H., et al., Sugar and wound healing Lancet, 1985, 2, 663-664.
8. Chirife J., et al., In-vitro study of bacterial growth inhibition in concentrated sugar solutions: microbiological basis for the use of sugar in treating infected wounds, Antimicrob. Ag. Chemother. 1983, 23, 766-773.
9. Winter G. D. and Scales J. T. Effect of air drying and dressings on the surface of a wound Nature, 1963, 197, 91-92.
10. Morgan D. Formulary of Wound Management Products ($3^{rd}$ edition), 1989, Clwyd Health Authority, Preswylfa, Hendy Road, Mold, Clwyd CH7 IPZ.

DESCRIPTION OF THE INVENTION

The present invention comprises a wound dressing for application to skin and mucous membranes, comprising at least 25% starch or polylactic acid and at least 25% of a mono- or disaccharide sugar, with a remainder comprising a compatible pharmaceutically acceptable formulation.

The resulting product is a powder which, when applied to a wound, absorbs wound secretions and acts as an antibacterial, likely due to the action of a high concentration of sugar. The product promotes healing, and aids in tissue regeneration. The power is applied to a wound in sufficient quantities to cake on the surface, forming a self-adherent dressing. The starch component acts as a matrix for tissue regeneration.

The product can be provided as a free powder, to be applied directly to a wound, or in the case of anal fissures and proctitis, the like, as a capsule containing the powder. The capsule is, for example, a standard gelatin capsule.

The starch may be, for example, cornstarch, which contains amylase and amylopectin, or other polysaccharides.

The starch may also be formed of saccharide monomer derivatives, such as sulfonated, acetylated, and other known biocompatible derivatives of saccharide monomers which form biocompatible polymers.

The disaccharide and polysaccharide (and/or polylactose) combination increases the blood flow within the tissues, which is important for tissue regeneration and aids in promoting a functional microvasculature, and ultimately, successful healing. A preferred sugar component is 10× powdered (confectioner's) sugar (sucrose).

The powder can be applied to various kinds of wounds, including ulcers, burns, avulsions, lacerations, surgical excisions, pilonodal cysts, and the like.

The powder is applied to wounds as necessary to absorb the secretions, for example at least twice daily. In a number of tests, with healing is visibly promoted within three days, and complete healing is generally observed within 7-10 days. In the case of open wounds, e.g., pilonidal operations, a longer period of treatment may be necessary.

In the case of a rectal suppository, the capsule is inserted in the rectum after bowel movements, and at least twice daily.

A dressing may be placed over the powder, for example a Telfa dressing. Telfa consists of a thin layer of absorbent cotton fibers, enclosed in a sleeve of poly(ethylene terephthalate) that is perforated in a regular pattern and sealed along two edges. The plastic film is present to prevent the dressing adhering to the surface of the wound, and is perforated to allow the passage of exudate from the wound into the body of the pad.

According to the present invention, since the starch absorbs the secretions, the body of the pad serves only a secondary function, and the combined dressing may be used on wounds which produce secretions which would normally be contraindicated for Telfa® alone.

It is therefore an object of the invention to provide a wound healing powder, comprising a sugar selected from the group consisting of one or more pharmaceutically acceptable monosaccharides and disaccharides, in an amount of at least 25% by weight of the powder mixture; and an absorbent agent which forms a bioabsorbable biocompatible matrix with wound secretions, comprising a polymer formed of one or more of saccharide or saccharide derivative monomers and lactic acid monomers, in an amount of at least 25% by weight of the powder mixture.

It is another object of the invention to provide a method for healing a wound on skin or mucous membranes, comprising administering a pharmaceutically acceptable powder to the wound comprising a sugar selected from the group consisting of one or more pharmaceutically acceptable monosaccharides and disaccharides, in an amount of at least 25% by weight of the powder mixture; and an absorbent agent which forms a bioabsorbable biocompatible matrix with wound secretions, comprising a polymer formed of one or more saccharide or saccharide derivative monomers and lactic acid monomers, in an amount of at least 25% by weight of the powder mixture, the powder being provided in sufficient quantity to form a cake on the wound from wound secretions and the powder.

The sugar may be present in an amount of at least 40% by weight and said absorbent agent is present in an amount of at least 40% by weight. In a preferred formulation, the sugar is present in an amount of about 50% by weight and the absorbent agent is present in an amount of about 50% by weight.

The sugar preferably comprises a finely powdered sucrose, e.g., 10× confectioner's sugar.

The absorbent agent preferably comprises cornstarch. The absorbent agent may also comprise polylactic acid, or a combination of starch and polylactic acid. Other absorbent agents may also be used, as are known in the art. A preferred starch is cornstarch.

The wound healing powder may be provided in a dissolvable capsule, e.g., a gelatin capsule, which holds at least 0.5 gram of powder, and more preferably 1 gram of powder.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A wound healing powder system adapted for treating wounds, comprising:
a free dry powder mixture comprising at least 40% by weight of a pharmaceutically acceptable sugar, and a pharmaceutically acceptable absorbent agent comprising at least one of a polysaccharide and polylactic acid, substantially without another antiseptic agent, said free dry powder being configured to form, when in contact with human physiological wound secretions from a skin or mucous membrane, a sufficiently low water activity, high osmotic pressure biocompatible bioabsorbable cake, which self-adheres to the wound, to achieve an antibacterial effect; and
a wound dressing, comprising an absorbent pad and a perforated polymer sheet, configured to cover the self-adherent cake on the wound and absorb excess exudate, without itself adhering to the cake.

2. The system according to claim 1, wherein the pharmaceutically acceptable sugar comprises finely powdered sucrose.

3. The system according to claim 1, wherein the pharmaceutically acceptable sugar comprises 10× sugar.

4. The system according to claim 1, wherein the pharmaceutically acceptable absorbent agent comprises cornstarch.

5. The system according to claim 1, wherein the pharmaceutically acceptable absorbent agent comprises polylactic acid.

6. The system according to claim 1, wherein the free flowing dry powder mixture further comprises polyethylene glycol.

7. The system according to claim 1, wherein the pharmaceutically acceptable absorbent agent is present in an amount of at least 40% by weight.

8. The system according to claim 1, wherein the pharmaceutically acceptable sugar is present in an amount of at least about 50% by weight.

9. The system according to claim 1, wherein the pharmaceutically acceptable absorbent agent is present in an amount of at least about 50% by weight.

10. The system according to claim 1, wherein the free dry powder mixture comprises 10× sugar and cornstarch.

11. The system according to claim 1, wherein the pharmaceutically acceptable sugar comprises, and the pharmaceutically acceptable absorbent agent comprises corn starch present in an amount of at least 25% by weight.

12. The system according to claim 1, wherein the system contains at least 0.5 gram of free dry powder.

13. A dry powder formulation for the treatment of wounds, comprising:
at least 40% by weight of one or more pharmaceutically acceptable monosaccharides or disaccharides substantially without another antiseptic agent, to generate an antibacterial effect of a cake formed with the dry power formulation and wound secretions by reducing water activity;
a sufficient proportion of a pharmaceutically acceptable absorbent agent comprising at least one of a polysaccharide and polylactic acid to form a self-adherent cake after being subject to contact with wound secretions;
said formulation being provided as free dry powder mixture, in a pharmaceutically acceptable form suitable for application to wounds of the skin or mucous membranes having wound secretions,
said formulation forming a self-adherent cake when administered on a wound having wound secretions, the formed cake having sufficient levels of the pharmaceutically acceptable monosaccharides or disaccharides achieves an antibacterial effect through reduction of water activity, and sufficient levels of the pharmaceutically acceptable absorbent agent to serve as a bioabsorbable biocompatible matrix in which tissue regeneration occurs.

14. The formulation according to claim 13, wherein the dry powder is free.

15. The formulation according to claim 13, wherein the dry powder is contained in a dissolvable capsule configured to dissolve when subject to wound secretions.

16. The formulation according to claim 13, wherein the pharmaceutically acceptable monosaccharides or dissacharides comprise finely powdered sucrose.

17. The formulation according to claim 13, wherein the pharmaceutically acceptable absorbent agent comprises cornstarch.

18. The formulation according to claim 13, wherein the pharmaceutically acceptable absorbent agent comprises polylactic acid.

19. The formulation according to claim 13, wherein the pharmaceutically acceptable absorbent agent is present in an amount of at least 40% by weight of the dry powder.

20. The formulation according to claim 13, further comprising a wound dressing, wherein the wound dressing comprises an absorbent pad and a perforated polymer sheet, configured to cover the cake on the wound and absorb excess exudate, without itself adhering to the cake.

21. The formulation according to claim 13, wherein the pharmaceutically acceptable absorbent agent is present in an amount of at least 25% by weight of the dry powder.

22. A method for treating wounds, comprising:

applying the dry powder according to claim 13, in free form, to a skin or mucous membrane wound having wound secretions, to form a self-adherent cake therewith, the pharmaceutically acceptable monosaccharides or disaccharides being present at antibacterial levels within the cake, and the pharmaceutically acceptable absorbent agent being present at sufficient levels to adhere the cake on the wound; and maintaining the self-adherent antibacterial dressing on the wound to serve as a bioabsorbable biocompatible matrix in which tissue regeneration occurs.

* * * * *

UNITED STATES PATENT AND TRADEMARK OFFICE
CERTIFICATE OF CORRECTION

| | | |
|---|---|---|
| PATENT NO. | : 8,252,335 B2 | Page 1 of 1 |
| APPLICATION NO. | : 11/938147 | |
| DATED | : August 28, 2012 | |
| INVENTOR(S) | : Philip A. Marraccini | |

It is certified that error appears in the above-identified patent and that said Letters Patent is hereby corrected as shown below:

Title Page, Item (12) and Item (76) Inventor should be amended to read:

-- Philip A. Marraccini -- instead of "Philip A. Maraccini"

Signed and Sealed this
First Day of January, 2013

David J. Kappos
*Director of the United States Patent and Trademark Office*